United States Patent [19]

van den Engh et al.

[11] Patent Number: 4,500,641

[45] Date of Patent: Feb. 19, 1985

[54] FLOW CYTOMETER FOR IDENTIFYING ALGAE BY CHLOROPHYLL FLUORESCENCE

[75] Inventors: Gerrit J. van den Engh; Barbara J. Trask, both of Bodegraven; Johannes W. M. Visser, Zevenhuizen, all of Netherlands

[73] Assignee: Nederlandse Centrale Organisatie voor Toegepast Natuurwetenschappelijk Onderzoek, The Hague, Netherlands

[21] Appl. No.: 360,430

[22] Filed: Mar. 22, 1982

[30] Foreign Application Priority Data

Mar. 23, 1981 [GB] United Kingdom ............... 8109068

[51] Int. Cl.$^3$ ...................... C12M 1/34; C12Q 1/29; C12Q 1/04; G01J 3/30
[52] U.S. Cl. ................... 435/291; 356/318; 435/4; 435/29; 435/34; 435/257
[58] Field of Search ............ 435/4, 34, 257, 291, 435/29, 32; 356/318, 367

[56] References Cited

U.S. PATENT DOCUMENTS

| | | | |
|---|---|---|---|
| 3,525,803 | 8/1970 | Smart | 356/367 X |
| 4,043,669 | 8/1977 | Gehatia et al. | 356/367 X |
| 4,061,543 | 12/1977 | Bean et al. | 435/291 X |
| 4,101,383 | 7/1978 | Wyatt et al. | 435/32 X |
| 4,203,670 | 5/1980 | Bromberg | 356/318 X |

FOREIGN PATENT DOCUMENTS

734270  5/1980  U.S.S.R.

Primary Examiner—David M. Naff
Attorney, Agent, or Firm—Armstrong, Nikaido, Marmelstein & Kubovcik

[57] ABSTRACT

Identification of algae in water samples is carried out with a flow cytometer having at least one high intensity light source to provide a light path such as a laser, means for passing the algae through the light path and a system of detectors arranged to measure chlorophyll fluorescence and at least two other parameters such as forward light scattering, perpendicular light scattering, backward light scattering, pulse length and/or shape of the scattered signals, fluorescence and pulse length and/or shape of the flourscence signals. In order to separate the light output from the flow cytometer into components which can yield useful measurements, a system of partially reflecting mirrors and dichroic mirrors is used. Preferably, the high intensity light source is two independent lasers having parallel light paths one of which is separated in a UV range and the other in an all lines mode.

6 Claims, 4 Drawing Figures

FLOW CYTOMETER FOR IDENTIFYING ALGAE BY CHLOROPHYLL FLUORESCENCE

BACKGROUND OF THE INVENTION a. Field of the Invention

The present invention relates to a new method for identifying algae in water samples and apparatus for use in that method.

b. Description of the Prior Art

The importance of algae as a measure of water quality has been recognized by C. M. Palmer, 1957, Algae as biological indications of pollution, Biol. of Water Poll. Trans. Seminar: Biol. Problems of Water Pollution, April 1956 Robt. A. Taft, San. Eng. Center, Cincinnati(Ohio), pp 60-69, and V. Sladacek, System of water quality from the biological point of view, Arch. Hydrobiol. Beiheft 7, pp. 1–218. However the application of that approach has been limited by the time and expertise needed to identify and count samples of a heterogeneous cell suspension of some 100 to 400 cells per sample by light microscopy. In addition this approach does not allow to obtain detailed information about the various species in the sample to the extent envisaged by the invention.

Flow cytometry has been used in recent years for studying mammalian cells. The principle of the flow cytometer is that cells are suspended in a liquid stream, whereupon this stream is passed through a laser beam. Light signals, providing information about cell size, structure and chemical composition are emitted from each cell and can be measured. Using measurements of the binding of fluorescent dyes after fixation of the cells, and thus killing the cells, and the light scattering of these cells, biologists have been able to measure various biological properties and to differentiate among functional populations of cells. (See M. R. Melamed, P. F. Mullaney and M. L. Mendelsohn, Flow Cytometry and Sorting, 1979, pp. 1-9 and 11-37, John Wiley & Sons, New York).

SUMMARY OF THE INVENTION

The inventors of the present invention have found that the limitations inherent to the above mentioned methods can be mitigated or avoided.

It is a primary object of the invention to provide detailed information about the species in a sample of a cell suspension as well as their type and number.

It is a further object of the invention to provide a method for analyzing plankton samples comprising phyto-plankton(algae), zoo-plankton and dead matter, in a very short time while obtaining detailed information about at least three parameters. Thus an exposure time to light of about 10 $\mu$sec. will usually provide a "fingerprint" of the cells and particles measured. Depending on the number of parameters involved, it will be possible to obtain a greater or lesser identification of the cells and particles concerned, and with respect to the cells also identification of the species and their abundance. By sampling water, it will thus be possible to obtain an indication about the purity of the sample taken, by comparing the picture of the sample with that of a sample of known purity. Whereas in non-polluted surface waters a large variety of species of algae will be encountered, in polluted surface waters only a few species will dominate. Such a control of water purity is of importance for surface waters, such as lakes, rivers, or even oceans, but also for municipal sewer systems, domestic water supplies, and samples of waste and/or cooling waters from industrial plants, and other effluents. The method according to the invention is especially of importance for detecting the passage of poisonous or otherwise polluting materials in a short period of time, which goes undetected for conventional sampling methods, if the passage takes place between two successive samplings, as the algae population will reflect the passing of these pollutants for a number of generations, usually for several days. Thus it will be possible to detect passage of pollutants even when this occurs between two successive samplings.

It is a further object of the invention to provide a method for identifying algae in water samples, wherein an aqueous fluid, comprising algae, is passed through an adapted flow cytometer without affecting the viability of living cells.

BRIEF DESCRIPTION OF THE DRAWINGS

The foregoing and other objects and advantages of the invention will become more readily apparent from the following description of the preferred embodiment of the adapted flow cytometer for use in the method according to the invention, but is not limited to that embodiment as taken in conjunction with the accompanying drawings, which are part hereof and wherein.

DESCRIPTION OF THE PREFERRED EMBODIMENT

Figure 1A:
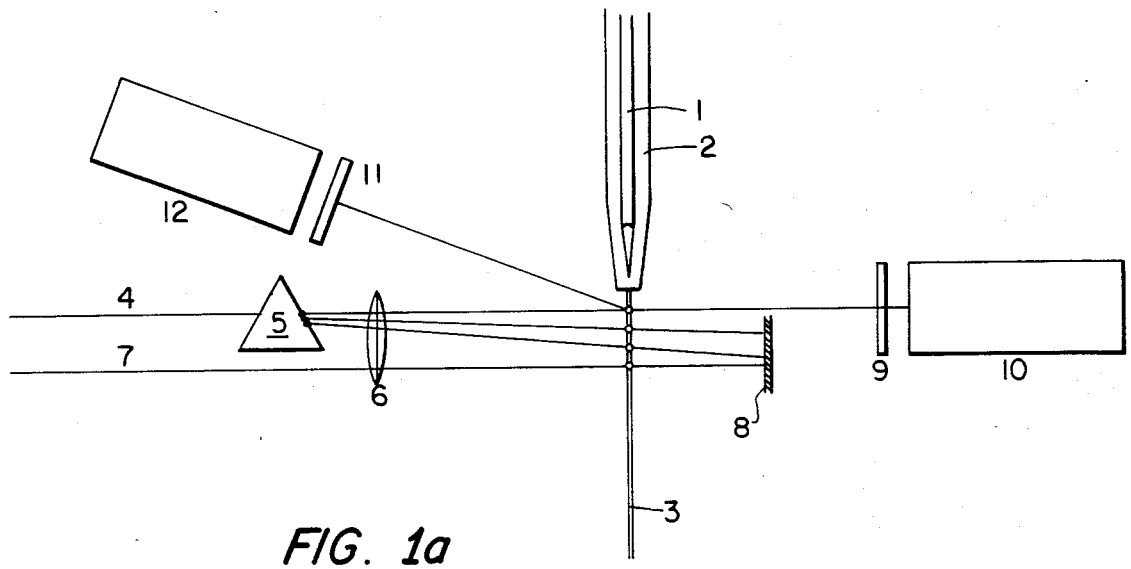
FIG. 1a represents a schematic side view.
Figure 1B:
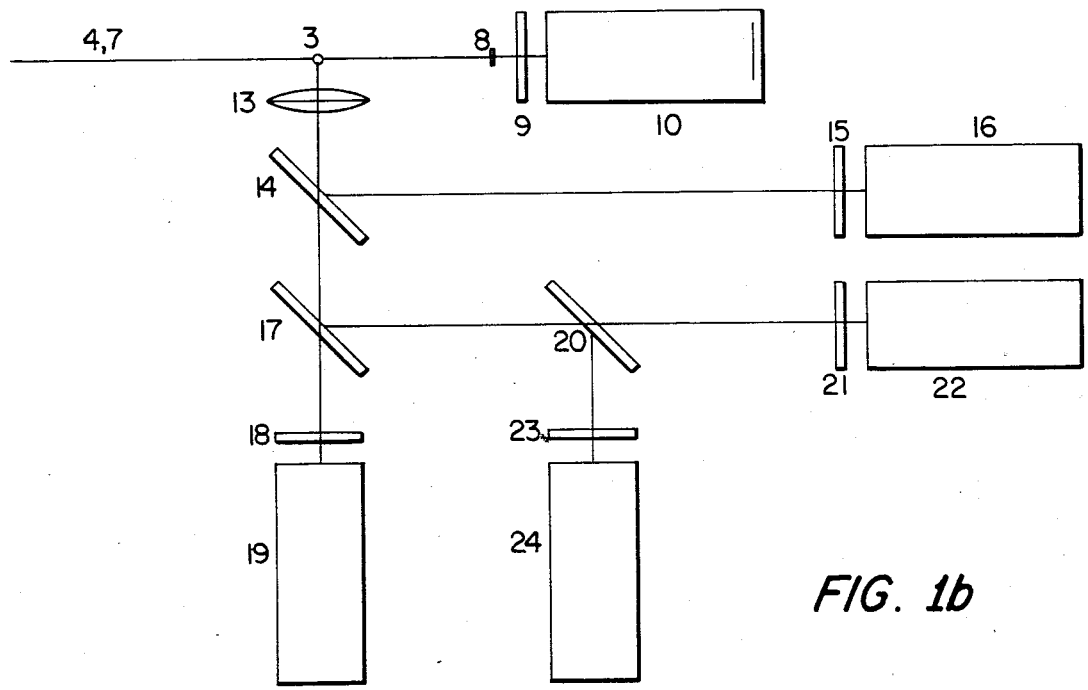
FIG. 1b represents a schematic top view of a flow cytometer in accordance with the present invention and FIG. 2a and FIG. 2b are graphical presentations of the measurements obtained by plotting the chlorophyll fluorescence against the forward light scattering and the perpendicular light scattering respectively.

In FIG. 1a representing a side view of a flow cytometer according to the invention, the following parts are shown in cooperative display: a sample injection tube 1, which avoids turbulence, and wherein an orientation of the particles is obtained, positioned within a cuvette 2, in which a sheath fluid is introduced to provide a liquid jet 3, comprising the sheath fluid in which the particles are suspended. Onto this liquid jet 3 are projected two laser beams at different levels, i.e. an argon laser 4, comprising all lines, which is first passed through a prism 5 and subsequently through a lens 6, before hitting the suspended particles. At a different level an argon laser 7, tuned to u.v. light, is passed through lens 6 before hitting the suspended particles. A laser stop 8 is positioned in line at a point beyond the liquid jet. In FIG. 1a incident light is reflected by the suspended particles in the liquid jet. The light scattered in forward direction is detected by forward light scatter detector 10 after the light has gone thrpugh a 515 nm band pass filter 9. Similarly the light scattered in backward direction is detected by a backward light scatter detector 12 after the light has gone through a 515 nm band pass filter 11. Whereas FIG. 1a provides a side view of a flow cytometer according to the invention, FIG. 1b provides a top view, showing the path of the perpendicular light scattering. Laser lights of argon ion lasers 4 and 7 hit liquid jet 3 and undeflected laser light is caught by laser stop 8. Perpendicularly scattered light passes through a lens 13 before hitting a 10% mirror 14, which reflects 10% of the incident light. The reflected light is detected by a perpendicular light scatter detector 16 after the light has gone through a 515 nm band pass filter 15. The light going through mirror 14 hits a dichroic mirror 17, which reflects light with a wavelength of 550 nm and shorter, whereas the higher wavelengths pass. The passing light is detected by a chlorophyll fluorescence detector 19 after passing a filter 18, cutting at 620 nm. The reflected light in turn hits another dichroic mirror 20, which again reflects the shorter wavelengths of 450 nm and less, while passing the longer one of 450 nm and more. The passing light is detected by a yellow fluorescence detector 22 after having passed through a yellow band pass filter 21.

The reflected light is detected by a DNA fluorescence detector 24 after having passed a blue band pass filter 23. Thus this three dimensional lay-out of the flow cytometer according to the invention makes it possible to obtain detailed information about the particles present in the liquid jet in a very short time. The method according to the invention can provide measurements of 100-200 samples per hour observing up to 10,000 cells per sample, against 1-2 samples per hour with presently known techniques. This result is obtained by channelling the signals from the detectors to a common computer, wherein these signals are combined for providing a multidimensional presentation. In this way 100-300 or more species of algae can be detected in a very short time, whereas analysis by microscope can provide such detailed information only after a much longer period of time.

Figure 2A:
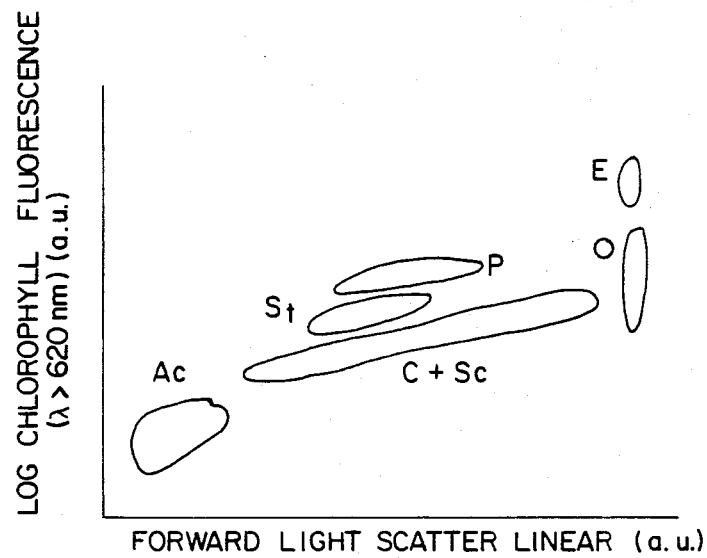
Figure 2B:
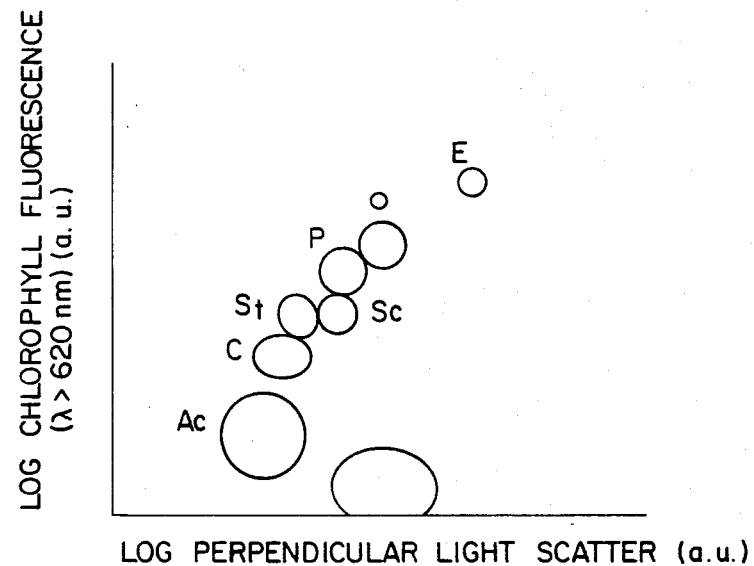

FIG. 2a and FIG. 2b are graphs of chlorophyll fluorescence plotted against forward light scattering and perpendicular light scattering respectively, for which data were obtained by the method according to the invention, using a previously prepared mixture of seven algae species. For identification purposes the data were initially taken for each one of the algae species separately. These graphs show the effectiveness of the analysis by the method according to the invention. The seven algae species used were:

Ac=Anacystis nidulans; C=Chlorella vulgaris; E=Euglena gracilis; O=Ochromonas danica; P=Phaedactylum tricornatum; Sc=Scenedesmus spp. and St=Stichococcus cylindricus.

In both graphs chlorophyll fluorescence (red, wavelength above 620 nm) is plotted, both axes being logarithmic. The excitation wavelength was 488 nm. In order to identify the clusters they were compared with the clusters of the individual algae species, obtained under otherwise identical conditions.

Thus the invention provides more specifically a method for identifying algae in water samples, wherein an aqueous fluid, comprising algae, is passed through an adapted flow cytometer, using at least one excitation wavelength and determining at least three parameters out of the following list of parameters using a high intensity light source for excitation: forward light scattering, perpendicular light scattering, backward light scattering, pulse length and/or shape of the scattered signals, chlorophyll fluorescence at different excitation wavelengths, fluorescence after staining of living cells with dyes, which do not affect the viability of the living cells, pulse length and/or shape of the fluorescence signals, at least one of the parameters being chlorophyll fluorescence, and the flow cytometer being adapted to detect all parameters to be measured.

According to another aspect of the invention, there is provided a flow cytometer for identifying algae, which comprises at least one high intensity light source, means for providing a liquid jet, detectors for forward light scattering, backward light scattering and a system for at least the chlorophyll fluorescence in light scattered perpendicularly which system comprises a lens, optionally a partially reflecting mirror, for example reflecting 10% of the incident lght, and for the light passing through said mirror a further, dichroic mirror and a chlorophyll fluorescence detector arranged to receive the light passing through said dichroic mirror; optionally a perpendicular light scattering detector for the light reflected by the partially reflecting mirror, a yellow fluorescence detector for the light reflected by said dichroic mirror, with appropriate band pass filters in front of each detector, and optionally a second dichroic mirror in front of the band pass filter of the yellow fluorescence detector, of which the reflected light is received by a DNA fluorescence detector with a band pass filter in front thereof, each detector providing signals from which data can be obtained.

The high intensity light source is preferably in the form of a laser, and more preferably is comprised of two independent lasers, one of which is operated in the UV range and the other in the all lines mode. Advantageously, the signals from the detectors are channelled to a common computer in which they are combined for providing a multi dimensional presentation.

Algae are much larger than mammalian cells, the latter being about 10 $\mu$m, whereas the algae range from 1 82 m to 2 mm. In order to be able to detect mammalian cells it is necessary to subject them to staining after chemical fixation. Algae comprise chlorophyll, which can provide chlorophyll fluorescence. The latter will however disappear by chemical fixation of algae. This advantage is taken of the naturally occurring pigments in algae to identify different classes and/or species. The fluorescence of the nucleaus and organelles of living cells after staining with special dyes, as discussed below, which can be used without chemical fixation of the cells, allows to distinguish them from dead cells and inorganic particles. In algae a special yellow fluorescence by an as yet unidentified organelle has been found at a wavelength of 530-560 nm after staining of the cells with the above-mentioned special dyes.

Apart from the above it is also possible to apply a charge onto the fluid, allowing for separation of the fluid stream by means of deflecting plates in at least two deflected streams, each stream comprising different groups of cells, apart from the main fluid stream, which passes undisturbed. The group of cells thus deflected, are comprised in the positively charged droplets, deflected in a particular direction, and the negatively charged droplets, deflected in the opposite direction; the uncharged (neutral) droplets pass undeflected. None of these operations affect the viability of living cells.

Though any high intensity light source is suitable for providing the desired information by its impact on the cells and particles onto which it is focussed, the most practical light source is a laser, such as a continuous argon ion laser of krypton ion laser, its beam having a width of at most 1 mm, preferably about 50 $\mu$m, with special preference for an argon ion laser with wavelengths in the UV-region (350-361 nm) and at 458, 476, 488, 496 and/or 515 nm. If more than one excitation wavelength is used, beams with different wavelengths should be focussed at different points.

In carrying out the method according to the invention certain precautions are either necessary or desirable. Thus the chances of clogging of the apertures in the apparatus used should be kept as small as possible, and if clogging does occur, correction should be easy. For a fluid stream in air it is possible to measure particles with a diameter of up to 120 μm. It is therefore necessary to remove larger particles; this may be done by sieving though other methods will be apparent to those skilled in the art. Alternatively much larger particles up to 1–2 mm can be accomodated in a flow cuvette measurement, thus avoiding the necessity of a pretreatment.

Reverting to the staining of the cells it is observed that in the experiments mentioned in this specification the cells were diluted to about $3\times10^6$ cells/ml in a suitable growth medium at pH 8. Dyes as mentioned hereafter were added in a concentration of 10 or 20 μg/ml, whereafter the cells were incubated for at least 1 hour a room temperature. It will be obvious to those skilled in the art that the data mentioned above are subject to variation, provided the viability of the cells is not affected to a substantial degree and the desired staining is obtained.

It should also be observed that any chlorophyll fluorescence is determined above 620 nm(red), any DNA fluorescence is determined after staining with the dyes mentioned below, without chemical fixation, at 375–500 nm(blue) and any as yet unidentified organelle is determined at 530–560 nm(yellow) in the preferred mode of the method according to the invention.

With respect to the various parameters obtainable by the method according to the invention, the following is observed: forward light scattering(FLS) provides information about the particle size, perpendicular light scattering(PLS) provides information about the particle structure, backward light scattering(BLS) provides information about particles with high refractive indices, e.g. inorganic particles, and in conjunction with FLS also about the shape of the particles, the pulse length of the scatter signals(duration) provides information about the length of the particles and the shape of the scatter signals(intensity) provides information about the width of the particles. The chlorophyll fluorescence at different wavelengths is a suitable paramater for distinguishing algae of different classes. This fluorescence can not be measured after chemical fixation(in the course of which the living cells are killed), and can only be measured on living cells.

Additional information can be obtained after staining the cells with special dyes, which can effectively be used without chemical fixation of living cells. As examples of these dyes are mentioned bisbenzimidazole derivatives, provided by Farbstoffwerke Hoechst as Hoechst 33258 and Hoechst 33342 and DAPI (hydroxystilbamine or 2-hydroxy-4,4'-diaminostilbene), which do no affect the viability of the living cells. After staining the fluorescence of the nucleus and other organelles of living cells is measured, this allowing for distinguishing living cells from dead cells and inorganic material. Duration and intensity of the fluorescence signals are determinative for length and width respectively of the particles concerned.

For a better distinction of the individual classes an/or species it is preferred to represent the results of the measurements plotted on a logarithmic scale, thus obtaining narrow bands for each one of the algae species.

In order to be able to differentiate between the various signals provided, mirrors are used: for some measurements partially reflecting mirrors, which are not selective with respect to wavelength are used and for others dichroic mirrors, i.e. mirrors which allow longer wavelengths(red) to pass, while reflecting the shorter wavelengths, are used.

In the flow cytometer as presented in the accompanying drawings many variations are possible, such as for example deletion of particular sections of the apparatus if it is not intended to measure the parameters provided by those particular sections. In the apparatus shown the lens was the objective of a microscope with magnification $10\times$ with long range, but any other lens or focussing mirror may be used instead. Similarly the prism may be replaced by a grating that may be holographic.

What we claim is:

1. Flow cytometer for identifying algae by chlorophyll fluorescence comprising:
   one high intensity light source comprising two independent lasers having parallel light paths one of which is operated in a UV range and the other in an all lines mode,
   a prism in the light path of the laser operated in the all lines mode,
   means for passing the algae through the light paths,
   detector means aligned with the light paths for detecting forward scatter and producing a signal,
   detector means for detecting backward scatter and producing a signal,
   means aligned perpendicularly to the light paths for detecting perpendicular scatter comprising a lens, a dichroic mirror, a chlorophyll fluorescence detector receiving light passing the dichroic mirror, a yellow fluorescence detector receiving light reflected by the dichoric mirror, and band pass filters in front of each detector; each detector producing a signal, and
   means for displaying the signals.

2. Flow cytometer according to claim 1, wherein said means for detecting perpendicular scatter further comprises a 10% mirror between the lens and the dichroic mirror reflecting 10% of incident light and means for measuring perpendicular scatter and producing a signal receiving light reflected by the 10% mirror.

3. Flow cytometer according to claim 1, wherein said means for detecting perpendicular scatter further comprises a second dichroic mirror between the dichroic mirror and the yellow fluorescence detector, a DNA fluorescence detector receiving light reflected by the second dichroic mirror and producing a signal, and a band pass filter between the second dichroic mirror and the DNA fluorescence detector.

4. Flow cytometer according to claim 2, wherein said means for detecting perpendicular scatter further comprises a second dichroic mirror between the dichroic mirror and the yellow fluorescence detector, a DNA fluorescence detector receiving light reflected by the second dichroic mirror and producing a signal, and a band pass filter between the second dichroic mirror and the DNA fluorescence detector.

5. Flow cytometer according to any one of claims 1, 2, 3 or 4 wherein said means for displaying comprises a common computer receiving the signals and producing a multidimensional presentation.

6. Flow cytometer according to claim 5, wherein the signals are plotted logarithmically.

* * * * *